United States Patent
Khoury

[11] Patent Number: 5,851,211
[45] Date of Patent: Dec. 22, 1998

[54] SUTURE NEEDLE HOLDER METHOD AND APPARATUS

[76] Inventor: Jamil Al Khoury, 1038 Craig Dr., San Jose, Calif. 95129

[21] Appl. No.: 841,422

[22] Filed: Apr. 22, 1997

[51] Int. Cl.⁶ .................................................. A61B 17/04
[52] U.S. Cl. ........................... 606/147; 606/207; 606/208
[58] Field of Search ................................... 606/147, 148, 606/205, 206, 207

[56] References Cited

U.S. PATENT DOCUMENTS

| 3,398,746 | 8/1968 | Abramson | 606/147 |
| 5,122,130 | 6/1992 | Keller | 606/207 |
| 5,201,743 | 4/1993 | Haber et al. | 606/147 |
| 5,290,309 | 3/1994 | Kothe | 606/207 |

*Primary Examiner*—Gary Jackson
*Attorney, Agent, or Firm*—Claude A.S. Hamrick; Oppenheimer w. Donnelly

[57] ABSTRACT

The invention is a needle holder for doing surgery in the oral cavity, especially those deep areas, and the hard to reach areas (palate, jaw joint, vestibular of the inferior and superior maxilla). The holder is an improved version of the present holders. It operates on the principle of off axis rotation and is held like a pencil or pen with the thumb and the index finger. It provides ease of use for the surgeon and better control in addition to an unobstructed field of view due to its smaller size when compared with the traditional holder. It does not employ locking teeth to hold the needle which prevents it from vibrating.

9 Claims, 4 Drawing Sheets

SUTURE NEEDLE HOLDER METHOD AND APPARATUS

BACKGROUND OF THE INVENTION

1. Field of the Invention

The present invention relates generally to surgical apparatus and more particularly to an improved needle holder of the type used by surgeons in suturing wounds in hard to reach areas such as the oral cavity.

2. Discussion of the Prior Art

There are various needle holders for suturing especially in the field of oral and maxillofacial surgery. All are based on one principle which is that the holder (stitching needle) is made up of 2 individual parts rotating around a single axis which facilitates central rotation.

The part above the joint is called the head and is made up of 2 clamps which hold the surgical needle. The head comes in various sizes and lengths to facilitate access to the area requiring suturing. The part below the joint is a dual armed holder terminating in winglets as in scissors or bent as in a "Mathieu holder". Since the needle needs to be held securely inside the clamps for delicate suturing, the two arms are serrated in opposite directions which clamp together when slid shut, thus holding the needle securely in place for suturing. To open, applying reverse pressure is enough to loosen the serrated edges and pry them apart, which releases the surgical needle.

The way to use the traditional holders is well known to surgeons. It is similar to the way scissors are handled (thumb in the upper ear of the upper hold, the middle finger in the lower ear, while the index finger is stretched along side the holder).

While using the holder, and while observing other surgeons using it too, I started noticing some negative aspects in the design which can hinder the surgeon and restrict him while suturing wounds in the oral cavity in deep areas of the mouth. These deficiencies are listed below:

1. The holder's size can restrict visibility especially when suturing in the back of the mouth.

2. It is difficult to control the movement of the instrument when doing delicate micro suturing in the oral cavity.

3. The serrations on the sides of the holder often cause the needle to vibrate while inside the tissues which leads to tearing them (needles with cutting edges) especially the tender tissues as is the case when dealing with the upper palate and the jaws. This has prompted some surgeons to cancel these serrations to prevent the tearing of the tissues.

Some surgeons are resorting to using both hands to secure the holder before opening it so the serration will not cause needle vibration, if any. Or the surgeon alters the way he holds the holder to the way one would hold a pencil rather than a pair of scissors. Even this method still poses difficulties.

Based on these difficulties arising from design deficiencies, and the difficulty that we, the surgeons, face while suturing using these holders, I started thinking about designing a simpler tool which allows a larger field of view while giving the surgeon better control of the suturing process.

OBJECTS OF THE INVENTION

Based on the aspects mentioned above, I focused on there points:

1. Changing the shape and reducing the size to ensure a wider field of view while suturing.

2. Finding an easier way to use the tool by surgeons; one which provides more control of the instrument and can ensure more precision.

3. Employment of an alternate movement principle and, subsequently, a different holder which eliminates the serration while still securing the needle in place.

Therefore, I invented a new advanced holder that can be described as follows:

SUMMARY OF THE INVENTION

Briefly, a presently preferred embodiment of the invention includes an elongated, generally cylindrical shaped body that terminates at one end in a first jaw-forming member, Between the cylindrical portion of the body and the first jaw member, a curvilinear camming surface is formed. Pivotally attached to the body at a point proximate the camming surface is another elongated member having one extremity forming a second jaw adapted to mate with the first jaw and another extremity forming a lever or handle generally parallel to the cylindrical body portion. Midway between the two extremities, a camming lobe is provided having an aperture through which a pivot pin extends, pivotally attaching the member to the body. The relationship between the camming lobe and the camming surface is such that as the second jaw is rotated about the pivot pin toward the first jaw, i.e., from an open position toward a closed position, the lobe progressively engages the camming surface with greater force, frictionally locking the jaws together.

IN THE DRAWING

DETAILED DESCRIPTION OF THE PREFERRED EMBODIMENTS

Figure 1:
FIG. 1 is a partially broken side view illustrating a first part of the needle holder in accordance with the present invention.
Figure 2:
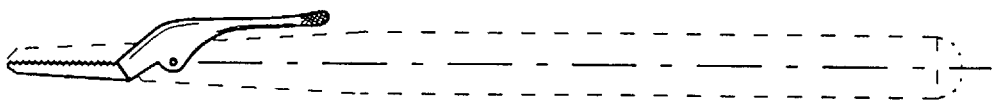
FIG. 2 is a side view of a second part of the needle holder.
Figure 3:
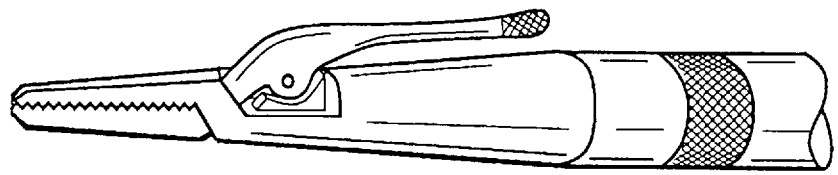
FIG. 3 is an enlarged view of the operational end of the holder with a portion thereof broken away to reveal operational detail.
Figure 4:
FIG. 4 is an exit cross section taken through the first part illustrated in FIG. 1.
Figure 5:
FIG. 5 is a longitudinal cross section taken through the second part illustrated in FIG. 2.

Referring now to FIGS. 1 and 2, it will be noted that the holder is made of two sections:

Section one illustrated at 10 in FIG. 1 is the main body of the holder. It is similar to a pen. It is narrower in the front end portion 11, then gradually thickens to a cylindrical shape 13 for the remainder of its length. It is made of:

a. Front end potion 11 is tapered and represents the upper clamp 22 of the holder with serrations at the internal surface 23.

b. Joint: This is placed behind the upper clamp 22 of the holder, within the main body of the instrument. It consists of a sliding camming surface 14 which receives the camming lobe 26 (FIG. 2) of the second section.

c. Handle: Made up of the back body 13 of the holder behind the joint cavity.

Figure 6:
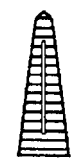
FIG. 6 is a plan view illustrating the serrated surfaces of the upper and lower jaw members.
Figure 7:
FIG. 7 is a top view of the operation end of the holder.
Figure 8:
FIG. 8 is a side view of the entire holder.

The second section is made of:

1. The lower clamp 20 which clamps fully on the upper section 22 and is shaped as a semi cone cut lengthwise. It has serrations that lock with their upper counterparts completely. (Added to that is a groove 21 (See FIG. 6) on the linear axis of both clamps.)

2. A joint disk or camming lobe 26 lies behind the lower clamp. This disk 26 slides on the mentioned sliding surface 14 around an axis 16.

3. A curved arm 24 in the shape of ~ connects with the joint disk 26 and extends along the lower clamp.

The movement principle is based on eccentric movement. The disk 26 rotates as an eccentric around its axis as its slides on a sliding surface 14 which initially is far from it. During the disk rotation and at a specific point on this surface, it will securely lock.

This contact will be calibrated based on the thickness of the needle used for suturing in the oral cavity. In addition, the flexibility of lower section arm 20 (lower clamp arm) helps in locking the needle in place based on the thickness of the needles used in oral surgery.

Figure 10:
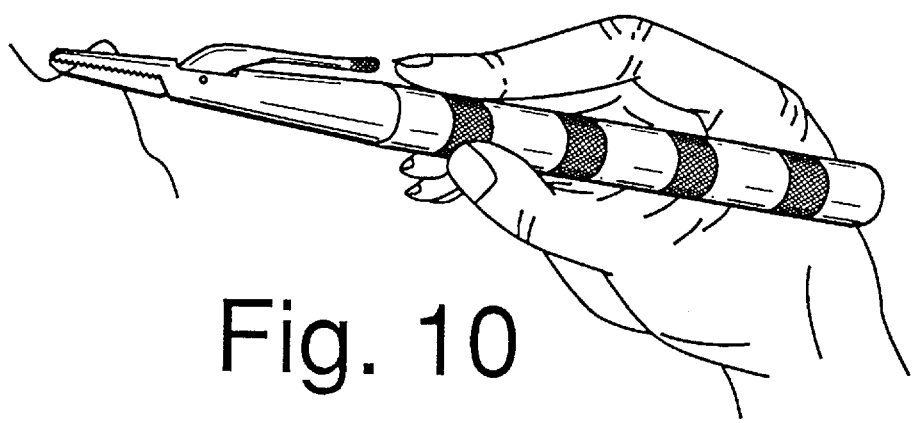
FIGS. 10 and 11 are illustrations depicting use of the holder.
Figure 11:
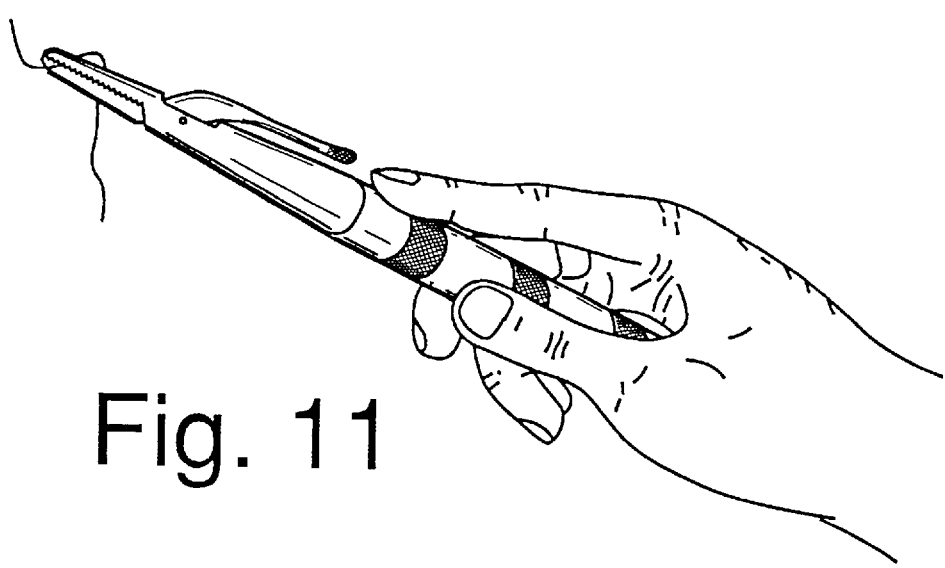

The technique used and illustrated in FIGS. 10 and 11 is based on the same technique used to hold a pencil with the thumb and the use of the thumb and the first finger. The first finger plays a major role in opening and closing the instrument using the smaller upper arm with an edge that curves upward to facilitate the placement of the tip of the index finger underneath it, and will open when slight pressure is exerted upwards on the small clamp. Applying pressure downwards will lock the instrument.

The illustrated holder may be used effectively for surgeries done in the oral cavity, especially for cleft palates and jaw alignments and all oral surgeries in the back of the mouth.

Figure 9:
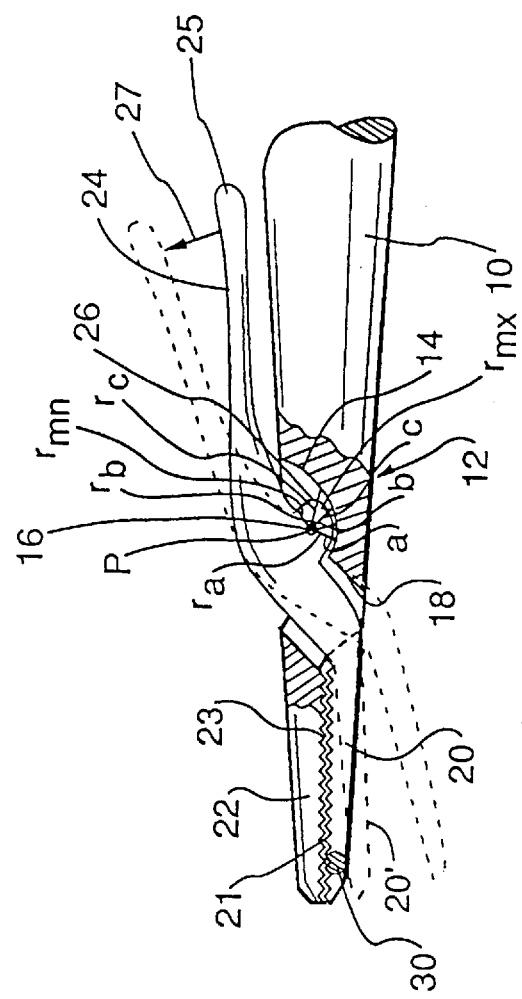
FIG. 9 is a depiction of the operative end of the holder, partially broken away to reveal operational detail.

Referring now to FIG. 9, the main body 10 of the holder is shown broken at 12 to reveal a camming surface 14 having a compound curvilinear surface defined by at least two segments a–b and b–c subtended by radii $r_a$ and $r_b$, and $r_b$ and $r_c$, respectively. In the preferred embodiment radius $r_a$=radius $r_b$ and radius $r_c$ is greater than the radii $r_a$ and $r_b$. Extending through a slot 18 in the main body 10 is a lower clamping member or jaw 20 having an upper surface 21 extending generally parallel to the lower surface 23 of an upper clamping member 22 when in its clamping position. The lower clamping member 20 forms an integral part of a handle member 24 including an elliptical or oval shaped camming lobe 26 having a central opening through which a shaft 16 passes.

Cam 26 has a maximum radius $r_{mx}$ and a minimum radius $r_{mn}$, where $r_{mn}$ is equal to or larger than $r_a$, $r_b$, and $r_{mn}$ is substantially less than $r_a$, $r_b$, such that when the lower clamping member 20 is rotated into its clamping position with surface 21 facing and either engaging or proximate to surface 23, the surface of cam 26 frictionally engages surface 14 in the region a–b, locking the lower clamping member 20 in position relative to the upper clamping member 22.

If a small object such as a needle, thread, suture or other means 30 is positioned between the members 20 and 22, it will be clamped therebetween as indicated by the dashed lines 20' and will remain locked therein so long as cam 26 is in engagement with the surface 14.

For some applications, it may be desirable to make the clamping members 20 and 22 somewhat flexible so that they exert a slight spring force upon the object 30 clamped therebetween. In addition, the surfaces 21 and 23 may be serrated or otherwise textured.

In order to unlock the clamping members, the user will apply finger pressure to the distal end of handle 24 at 25, rotating handle 24 upwardly in the direction indicated by arrow 27 and causing lower jaw member 20 to rotate downwardly as the handle member rotates about pivot 16. Since cam 26 is oval and has a changing diameter, and surface 14 has a compound curvature, it will be appreciated that as handle 24 is lifted, cam 26 will rotate out of engagement with surface 14 so that the lower clamping member and handle 24 can be freely rotated.

It will, of course, also be appreciated that other frictional clamping mechanisms can be substituted for the eccentric cam 26 and compound curved camming surface 14. For example, cam 26 could be by a tab having tapered side surfaces that engage either a single side surface or facing side surfaces in holder 10 to accomplish a similar result; namely, frictionally locking the jaws together over a small clamping angle.

What I claim is:

1. A clamping means for use in surgical applications, comprising:

an elongated holder having a first clamping member extending from one extremity thereof, said holder having means forming a first camming surface;

pivot means disposed proximate said camming surface; and an elongated member pivotably attached to said holder by said pivot means and having a portion at one end thereof forming a second clamping member for rotation into facing relationship with said first clamping member and the opposite extremity thereof forming a handle for facilitating rotation of said second clamping member about said pivot means, said elongated member further including a camming means for frictionally engaging said camming surface as said second clamping member is rotated towards said first clamping member thereby locking said second clamping member relative to said first clamping member whereby a surgical needle may be clampingly engaged between said first and second clamping members.

2. A clamping means as recited in claim 1 wherein the facing surfaces of said first and second clamping members are serrated.

3. A clamping means as recited in claim 1 wherein said first camming surface has a compound curvilinear configuration partially circumscribing said pivot means.

4. A clamping means as recited in claim 3 wherein said camming means is in the form of an oval shaped lobe and the surface thereof has a relationship to said first camming means such that as said second clamping member is rotated towards said first clamping member, the frictional engagement between the surface of said lobe and said camming surface increases.

5. A clamping means as recited in claim 1 wherein said camming means is in the form of an oval shaped lobe and the surface thereof has a relationship to said first camming means such that as said second clamping member is rotated towards said first clamping member, the frictional engagement between the surface of said lobe and said camming surface increases.

6. A clamping means as recited in claim 1 wherein said elongated member extends through a passageway open at one extremity above said pivot means and open at an opposite extremity beneath said first clamping member.

7. A clamping means as recited in claim 1 wherein said handle is deformed so that it lies substantially parallel to the exterior surface of said holder when said second clamping member is in close facing relationship to said first clamping member.

8. A clamping means as recited in claim 1 wherein said holder is of generally cylindrical cross section along a substantial portion of its length, the remaining portion of its length being convergingly tapered to terminate in said first clamping member.

9. A clamping means as recited in claim 1 wherein said first and second clamping means are tapered from a first transverse width proximate said pivot means to a second transverse width less than said first width at the distal extremities thereof.

* * * * *

UNITED STATES PATENT AND TRADEMARK OFFICE
CERTIFICATE OF CORRECTION

PATENT NO : 5,851,211
DATED : 12/22/98
INVENTOR(S): Jamil Alkhoury

It is certified that error appears in the above-identified patent and that said Letters Patent is hereby corrected as shown below: On the title page,

[76] Inventor: Jamil Alkhoury, 1038 Craig Dr., San Jose, Calif. 95129

Title page item 19 & item 76

Signed and Sealed this

Fourth Day of May, 1999

Attest:

Q. TODD DICKINSON

*Attesting Officer*    *Acting Commissioner of Patents and Trademarks*